United States Patent [19]

Engel

[11] 4,395,567
[45] * Jul. 26, 1983

[54] 1R,CIS-3-(2-HALO-3,3,3-TRIFLUORO-1-PROPENYL)-2,2-DIMETHYLCYCLOPROPANECARBOXYLIC ACID DERIVATIVES

[75] Inventor: John F. Engel, Washington Crossing, Pa.

[73] Assignee: FMC Corporation, Philadelphia, Pa.

[*] Notice: The portion of the term of this patent subsequent to Dec. 9, 1997, has been disclaimed.

[21] Appl. No.: 327,839

[22] Filed: Dec. 7, 1981

Related U.S. Application Data

[63] Continuation-in-part of Ser. No. 221,656, Dec. 31, 1980, Pat. No. 4,333,950.

[51] Int. Cl.³ .......................................... C07C 69/743
[52] U.S. Cl. .................................... 560/124; 424/305
[58] Field of Search ........................................ 560/124

[56] References Cited

U.S. PATENT DOCUMENTS 4,238,505 12/1980 Engel ................................. 424/305

Primary Examiner—Richard Raymond
Attorney, Agent, or Firm—Robert L. Anderson; H. Robinson Estell

[57] ABSTRACT 1R,cis-trifluoromethylethenylcyclopropanecarbonyl compounds of the formula

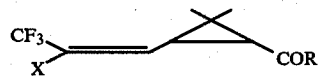

in which X is halogen and R is halogen, hydroxy, lower alkoxy or an optionally substituted 1,1'-biphenyl-3-methyloxy group, their method of preparation and utility as insecticides and intermediates therefore are described and exemplified.

3 Claims, No Drawings

1R,CIS-3-(2-HALO-3,3,3-TRIFLUORO-1-PROPENYL)-2,2-DIMETHYLCYCLO-PROPANECARBOXYLIC ACID DERIVATIVES

The present application is a continuation-in-part of copending U.S. Ser. No. 221,656, filed Dec. 31, 1980, now U.S. Pat. No. 4,333,950, the disclosure of which is incorporated herein by reference.

The present invention is directed to an optically active cyclopropanecarboxylic acid, acid halide, and lower alkyl ester, to insecticidal and acaricidal pyrethroid esters made therefrom, and to an insecticidal and acaricidal method and composition. In particular the invention relates to 1R,cis-3-(2-halo-3,3,3-trifluoro-1-propenyl)-2,2-dimethylcyclopropanecarboxylic acid, acid halide, lower alkyl ester, and insecticidal derivatives thereof.

Pyrethrins, naturally occurring extracts of crysanthemum flowers, have long been of interest as insecticides. Since elucidation of the structures of these compounds, synthesis efforts have been directed toward preparation of related compounds having enhanced insecticidal activity and improved stability toward air and light. Since a prerequisite for insecticidal activity and pyrethroids is the presence of one molecule of an appropriate acid moiety and an appropriate alcohol moiety, research in the art has been directed toward novel acid and/or alcohol radicals. A significant advance in pyrethroid acid research was the discovery by Elliott of a highly active group of compounds in which the acid moiety is a 3-(2,2-dichloroethenyl)-2,2-dimethylcyclopropanecarboxyl group. More recently it has been found that replacement of one of the halogen atoms on the ethenyl group with a perhaloalkyl group results in perhaloalkylethenylcyclopropanecarboxylates having substantially improved insecticidal properties over those exhibited by Elliott's dihaloethenylcyclopropanecarboxylates.

The parent applications and patents referred to above disclose various perhaloalkylcyclopropanecarboxylates, and describe generally the various possible isomeric and steric configurations of such compounds.

It has now been found that the 1R,cis isomer of 3-(2-halo-3,3,3-trifluoro-1-propenyl)-2,2-dimethylcyclopropanecarboxylic acid, when esterified with certain optionally substituted 1,1-biphenyl methanols, produces a pyrethroid ester having greatly enhanced insecticidal properties over the corresponding esters of the racemic acid. The racemic acid and esters are disclosed in U.S. Pat. No. 4,238,505, issued Dec. 9, 1980.

In this application, the term "lower" as applied to an aliphatic carbon group means having 1 to 6 carbon atoms, preferably 1 to 4 carbon atoms. The term "halo" or "halogen" means bromine, chlorine, or fluorine. The term "insecticide" is used in its broadest sense to include compounds possessing activity against true insects, acarids, and other household, veterinary or crop pests of the philum Arthropoda. These definitions are applicable throughout the specification and claims except where a contrary meaning is clearly indicated.

Accordingly, the present invention provides a 1R,cis-trifluoromethylethenylcyclopropanecarbonyl compound of formula I:

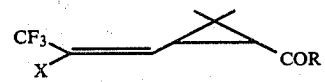

in which X is a halogen atom, R is a halogen atom, a hydroxyl group, a lower alkoxy group, or an alcohol residue of formula II:

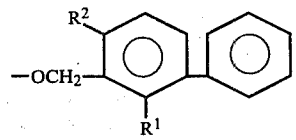

in which $R^1$ and $R^2$ are independently hydrogen, lower alkyl or halogen.

The compounds in which R is halogen, hydroxy, or lower alkoxy are intermediates to the insecticidal compounds in which R is as shown in formula II. The preferred compounds are those in which $R^1$ and $R^2$ are each hydrogen, or in which $R^1$ is methyl and $R^2$ is hydrogen, or in which $R^1$ and $R^2$ are each methyl.

Cyclopropanecarboxylates exist as cis and trans geometrical isomers; the carbonyl and substituted vinyl groups at the 1 and 3 positions of the cyclopropane ring are either cis or trans with respect to each other. Preparation of such compounds will usually yield a mixture of cis and trans isomers, designated cis, trans, in which the ratio of cis to trans may vary over a wide range. For purposes of this specification the designation cis and trans are assigned in accordance with P. E. Burt, et al., *Pestic. Sci.*, 5, 791-799 (1974). The compounds of this invention are cis isomers having the R configuration at $C_1$ of the cyclopropane ring. The 1R,cis acids of this invention may be prepared by resolving the corresponding racemic cis acid, utilizing, for example, an optically active amine, as is well known to those skilled in this art.

The insecticidal compounds of this invention may be prepared by reacting a salt of the 1R,cis carboxylic acid of formula I (R=OM, wherein M is an alkali metal or ammonium group) with a compound of the formula III

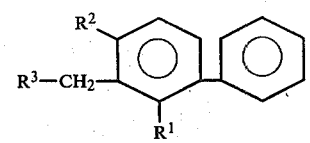

in which $R^1$ and $R^2$ are as defined above and $R^3$ is a good leaving group, such as, chloro, bromo, methanesulfonyloxy, p-toluenesulfonyloxy or a lower trialkylaminio halide.

The insecticidal compounds may also be prepared by converting the 1R,cis carboxylic acid to the corresponding acid halide of formula I (R=halogen), for example by reacting the acid with a halogenating agent such as thionyl chloride or oxalyl chloride, then reacting the resulting acid halide with a compound of formula III in which $R^1$ and $R^2$ are as defined above and $R^3$ is hydroxy, preferably in the presence of a hydrogen halide acceptor.

In addition, the 1R,cis carboxylic acid of formula I (R=OH) may be esterified by reaction of a lower alkanol, preferably methanol or ethanol, to form the lower alkyl ester of I, in which R is lower alkoxy, then transesterifying the resulting lower alkyl ester in an inert solvent with a compound of formula III in which $R^1$ and $R^2$ are as defined above and $R^3$ is hydroxy. Other standard methods of esterification would also be applicable in the preparation of the present insecticidal esters.

The following examples illustrate preparation of the compounds of this invention.

EXAMPLE 1

Synthesis of (2-methyl-[1,1'-biphenyl]-3-yl)-methyl 1R-cis-3-(2-chloro-3,3,3-trifluoro-1-propenyl)-2,2-dimethylcyclopropanecarboxylate

(a) Resolution of cis-3-(2-chloro-3,3,3-trifluoro-1-propenyl)-2,2-dimethylcyclopropanecarboxylic acid A stirred solution of 15.0 grams (0.062 mole) of cis-3-(2-chloro-3,3,3-trifluoro-1-propenyl)-2,2-dimethylcyclopropanecarboxylic acid in 250 ml of toluene was warmed to 50°–60° C. and 8.5 grams (0.070 mole) of (−) α-methylbenzyl amine was added dropwise during a 30 minute period. The reaction mixture was then allowed to cool to ambient temperature where it stood for 16 hours. A solid, weighing 16.7 grams, m.p. 167°–172° C., was collected by suction filtration. The solid was dissolved in 100 ml of hot ethanol. The solution was cooled slowly by turning off the heat source and wrapping the flask containing the solution with a towel. No crystals had formed in the solution after it had cooled to ambient temperature. The solution was placed in a refrigerator causing a solid to crystallize in the form of white needles. The solid was collected by suction filtration to give 7.6 grams of material, m.p. 174°–175° C. The solid was recrystallized from 65 ml of hot ethanol to give 2.1 grams of the amine salt of 1R-cis-3-(2-chloro-3,3,3-trifluoro-1-propenyl)-2,2-dimethylcyclopropanecarboxylic acid; m.p. 175°–176.5° C. The salt was dissolved in 50 ml of diethyl ether and placed in a separatory funnel. The solution was shaken with 40 ml of 0.5 N sodium hydroxide until the solution was clear. The diethyl ether layer was separated and the basic aqueous layer acidified with 15 ml of 2 N hydrochloric acid. The mixture was extracted with two portions of 25 ml each of diethyl ether. The combined extracts were dried with magnesium sulfate and filtered. The filtrate was concentrated under reduced pressure to give 1.2 grams of 1R-cis-2-(2-chloro-3,3,3-trifluoro-1-propenyl)-2,2-dimethylcyclopropanecarboxylic acid, m.p. 112°–112.5° C. The optical purity of the acid, was determined to be at least 94% 1R-cis utilizing a chiral lanthanide shift reagent in accordance with the methods set forth in H. L. Goering et al., JACS. 96, 7842 (1974) and E. L. Plummer et al., J. Chem. ECOL., 2, 307 (1976).

(b) Synthesis of 1R-cis-3-(2-chloro-3,3,3-trifluoro-1-propenyl)-2,2-dimethylcyclopropanecarbonyl chloride A stirred solution of 1.0 gram (0.004 mole) of 1R-cis-3-(2-chloro-3,3,3-trifluoro-1-propenyl)-2,2-dimethylcyclopropanecarboxylic acid in 50 ml of toluene was warmed to 60° C. and 1.0 gram (0.008 mole) of oxalyl chloride was added. The reaction mixture was heated at 60° C. for 5.25 hours then cooled to ambient temperature. The reaction mixture was concentrated under reduced pressure to a residual oil. The oil was dissolved in 15 ml of dry toluene and again concentrated under reduced pressure to give 1.0 gram of 1R-cis-3-(2-chloro-3,3,3-trifluoro-1-propenyl)-2,2-dimethylcyclopropanecarbonyl chloride as an oil. The oil was used without further purification.

(c) Synthesis of (2-methyl-[1,1'-biphenyl]-3-yl)methyl 1R-cis-3-(2-chloro-3,3,3-trifluoro-1-propenyl)-2,2-dimethylcyclopropanecarboxylate To a stirred mixture of 0.8 gram (0.004 mole) of (2-methyl-[1,1'-biphenyl]-3-methanol and 0.3 ml of pyridine was added 1.0 gram (0.004 mole) of 1R-cis-3-(2-chloro-3,3,3-trifluoro-1-propenyl)-2,2-dimethylcyclopropanecarbonyl chloride in 25 ml of toluene. A solid precipitate formed immediately. The reaction mixture was stirred at ambient temperature for 16 hours, then poured into 50 ml of 2 N hydrochloric acid. The mixture was shaken and the organic layer separated. The organic layer was washed with one portion of 25 ml of an aqueous solution saturated with sodium chloride. The organic layer was dried with magnesium sulfate and filtered. The filtrate was placed on a column of 100 grams of silica gel. Elution was accomplished with toluene. The appropriate fraction was concentrated under reduced pressure to give 1.11 grams of (2-methyl-[1,1'-biphenyl]-3-yl)methyl 1R-cis-3-(2-chloro-3,3,3-trifluoro-1-propenyl)-2,2-dimethylcyclopropanecarboxylate. Gas chromatographic analysis indicated >98% purity. The ir spectrum was consistent with the proposed structure.

nmr (CCl$_4$): 1.32 (6H,2), 2.12 (2H,m), 2.21 (3H,s), 5.17 (2H,s), 6.95 (1H,d).

In the method aspect of this invention, an effective insecticidal or acaricidal amount of the compound of formula I wherein $R^2$ is the alcohol residue of formula II is applied to the locus where control is desired, i.e., to the insect or acarid itself or to the foliage or seeds of agricultural plants. The compounds are useful for the control of household, veterinary, and crop pests of the phylum Arthropoda, and may be applied as technical material or as formulated product. Typical formulations include compositions of the active ingredient in combination with one or more agriculturally acceptable carriers or extenders, preferably with a surface active agent, and optionally with other active ingredients. Suitable formulations include granules, powders, or liquids, the choice varying with the type of pest and environmental factors present at the particular locus of infestation. Thus, the compounds may be formulated as granules of various sizes, as dusts, as wettable powders, as emulsifiable concentrates, as solutions, as dispersions, as controlled release compositions, and the like. A typical formulation may vary widely in concentration of active ingredient depending upon the particular agent used, the additives and carriers used, other active ingredients, and the desired mode of application. With due consideration to these factors the active ingredient of a typical formulation may, for example, be suitably present at a concentration of about 0.01% up to about 99.5%, preferably 0.1% up to 90% or 95%, of the formulation. An agriculturally acceptable carrier may comprise about 99.5% by weight to as low as about 0.5% by weight of the formulation. Compatible surface active agents, if employed in a formulation, may be present at various concentrations, suitably in the range of 1 to 30% by weight of the formulation.

The formulation may be used as such or diluted to a desired use dilution with a diluent or carrier suitable for facilitating dispersion of the active ingredients. A concentration of the active ingredient in the use dilution may be in the range of 0.001% to about 50%, preferably up to about 10% by weight.

Many variations of spraying, dusting, and controlled or slow release compositions of a type known in the art may be used by substituting or adding an insecticidal compound or compounds of this invention into the compositions known or apparent to the art.

The insecticidal or acaricidal compounds of this invention may be formulated and applied with other compatible active agents including nematicides, insecticides, acaricides, fungicides, plant regulators, herbicides, fertilizers, and the like.

In applying these compounds, whether alone or with other agricultural chemicals, an effective insecticidal or acaricidal amount of the active ingredient must be applied. While the application rate will vary widely depending on the choice of compound, formulation, mode of application, plant species being protected, planting density and other like factors, a suitable use rate for agricultural crops may be in the range of 0.005 to 3 k/ha, preferably 0.01 to about 1 k/ha.

The insecticidal or acaricidal compounds of this invention were tested for pesticidal activity as described below.

EXAMPLE 2

Topical Application Test

Two replicates of ten larvae of each test species were employed for each test compound. A petri dish lined with a piece of filter paper, and containing a food source was employed for each replicate. A one microliter droplet of a solution of test compound in acetone, at various dosage levels in the range of 15 to 2 nanograms/insect, was applied to the second or third dorsal thoracic segment of each larva. The insects employed were southern armyworm (*Spodoptera eridania* [Cram.]), the Mexican bean beetle (*Epilachna varivestis* Muls.). The test compounds were the compound of Example 1, and the corresponding racemic ester, (2-methyl-[1,1'-biphenyl]-3-yl)-methyl 1RS,cis-3-(2-chloro-3,3,3-trifluoro-1-propenyl)-2,2-dimethylcyclopropanecarboxylate. The tests were read twenty-four hours after application of the toxicant solution, and the ratio of the potency of the compound of Example 1 to the potency of the racemic ester was calculated. The compound of Example 1 was 1.7 times as active as the racemic ester against Southern armyworm and 1.6 times as active against Mexican bean beetle.

I claim:

1. A 1R,cis-trifluoromethylethenylcyclopropanecarbonyl compound of the formula

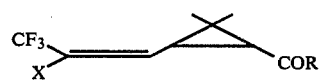

in which X is halogen, R is an alcohol residue of the formula

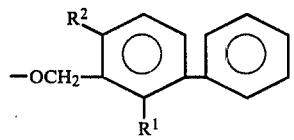

in which $R^1$ and $R^2$ are independently hydrogen, lower alkyl or halogen.

2. The compound of claim 1 in which R is the alcohol residue of formula II.

3. The compound (2-methyl-[1,1'-biphenyl]-3-yl)methyl 1R,cis-3-(2-chloro-3,3,3-trifluoro-1-propenyl)-2,2-dimethylcyclopropanecarboxylate.

* * * * *